United States Patent
Wang et al.

(10) Patent No.: US 12,186,323 B2
(45) Date of Patent: Jan. 7, 2025

(54) COMBINATION DRUGS OF HYPOXANTHINE AND HUMAN IMMUNOGLOBULIN

(71) Applicants: Institute of Blood Transfusion, Chinese Academy of Medical Sciences, Sichuan (CN); Institute of Radiation Medicine, Chinese Academy of Medical Sciences, Tianjin (CN); Shanghai RAAS Blood Products Co., Ltd., Shanghai (CN)

(72) Inventors: Zongkui Wang, Sichuan (CN); Ming Cui, Tianjin (CN); Changqing Li, Sichuan (CN); Jun Xu, Shanghai (CN); Lu Cheng, Shanghai (CN)

(73) Assignees: Institute of Blood Transfusion, Chinese Academy of Medical Sciences, Sichuan (CN); Institute of Radiation Medicine, Chinese Academy of Medical Sciences, Tianjin (CN); Shanghai RAAS Blood Products Co., Ltd., Shanghai (CN)

( * ) Notice: Subject to any disclaimer, the term of this patent is extended or adjusted under 35 U.S.C. 154(b) by 67 days.

(21) Appl. No.: 17/811,715

(22) Filed: Jul. 11, 2022

(65) Prior Publication Data

US 2022/0339158 A1 Oct. 27, 2022

(30) Foreign Application Priority Data

Jul. 13, 2021 (CN) .......................... 202110791985.4

(51) Int. Cl.
*A61K 31/522* (2006.01)
*A61K 9/00* (2006.01)
*A61K 39/395* (2006.01)
*A61P 43/00* (2006.01)

(52) U.S. Cl.
CPC .......... *A61K 31/522* (2013.01); *A61K 9/0019* (2013.01); *A61K 39/395* (2013.01); *A61P 43/00* (2018.01)

(58) Field of Classification Search
CPC .... A61K 31/33; A61K 31/395; A61K 31/522; A61K 9/0019; A61K 39/395; A61K 2039/505; A61K 39/39525; A63B 2213/001; A61P 43/00; A61P 1/00; A61P 7/00; A61P 29/00; A61P 37/04; A61P 39/00; A61P 35/00; Y02A 50/30; C07K 16/06
See application file for complete search history.

(56) References Cited

PUBLICATIONS

George, K.C. et al, Caffeine protects mice against whole-body lethal dose of gamma irradiation, 1999, Journal of Radiological Protection, vol. 19, No. 2, 171-176. (Year: 1999).*

(Continued)

*Primary Examiner* — Noble E Jarrell
*Assistant Examiner* — Richard Grant Peckham
(74) *Attorney, Agent, or Firm* — NKL Law; Allen Xue

(57) ABSTRACT

A combination drug contains hypoxanthine and human immunoglobulin (HIg). HIg has a therapeutic effect on radiation injuries, and the combination of hypoxanthine and HIg can further enhance this therapeutic effect. The combination drug can be administered to patients undergoing radiotherapy and to those who accidentally have excessive irradiation.

9 Claims, 4 Drawing Sheets

(56) References Cited

PUBLICATIONS

Makhloufi, A. et al, Converting Caffeine to Electronically Different N-Heterocyclic Carbenes with a Hypoxanthine Backbone, 2012, Organometallics, vol. 13, 7272-7277. (Year: 2012).*

Nikitin, A. I. et al, Research into the use of protective agents in the case of combined radiation and chemical injury, 2017, Bali Medical Journal, vol. 6, No. 2, 341-344. (Year: 2017).*

Burkhard Ludewig and Mathias W. Hoffmann, Adoptive Immunotherapy (methods and protocols), Published 2005 Humana Press Inc. (Chapter 26, pp. 403-408 (Year: 2005).*

Yin, C. et al, Hypoxanthine Induces Muscular ATP Depletion and Fatigue via UCP2, 2021, Frontiers in Physiology, vol. 12, Article 647743, pp. 1-13. (Year: 2021).*

Novaretti, M. C. et al, Immunoglobulin: production, mechanisms of action and formulations, 2011, Revista Brasileira de Hematologia e Hemoterapia. vol. 33, No. 5, 377-382. (Year: 2011).*

Weisdorf, D. et al, Acute radiation injury: contingency planning for triage, supportive care, and transplantation, 2006, Biology of blood and marrow transplantation, vol. 6, 672-682. (Year: 2006).*

Taïeb, S. et al, Effective use of argon plasma coagulation in the treatment of severe radiation proctitis, 2001, Diseases of the Colon and Rectum, vol. 44, No. 12, 1766-1771. (Year: 2001).*

Andaluz-Ojeda, D. et al, Early levels in blood of immunoglobulin M and natural killer cells predict outcome in nonseptic critically ill patients, 2013, Journal of Critical Care, vol. 28, No. 6, 1110.e7-1110.e10. (Year: 2013).*

Nemkov, T. et al, Hypoxia modulates the purine salvage pathway and decreases red blood cell and supernatant levels of hypoxanthine during refrigerated storage, 2018, Haematologica, vol. 103, No. 2, 361-372. (Year: 2018).*

Rzyman, W. et al, The influence of blood transfusion on survival in operated non-small cell lung cancer patients, 2003, The Journal of Thoracic and Cardiovascular Surgery, vol. 126, No. 3, 755-760. (Year: 2003).*

\* cited by examiner

COMBINATION DRUGS OF HYPOXANTHINE AND HUMAN IMMUNOGLOBULIN

TECHNICAL FIELD

The present invention belongs to the field of biopharmaceuticals.

BACKGROUND TECHNOLOGY

Cancer is the second leading cause of death in human beings. Radiotherapy is a widely used means for the treatment of cancer, and its contribution ratio to cancer treatment is as high as 18%, which is second only to surgery and significantly higher than chemotherapy and biological therapy. However, it is inevitable that radiotherapy is accompanied by varying degrees of acute and chronic organ damage represented by inflammation and fibrosis, respectively. Specifically, radiotherapy for head and neck tumors often leads to oral mucositis; radiotherapy for thoracic tumors often leads to chronic pneumonia; and radiotherapy for abdominal and pelvic tumors often leads to diarrhea, chronic enteritis, intestinal obstruction, etc. However, hematopoietic injury such as leukocytopenia and myeloid deviation as well as digestive tract injury such as enteritis and intestinal obstruction are very common complications in radiotherapy for multiple cancers, which will halt radiotherapy prematurely, degrade patient life quality and even cause death. Increasing the dose of radiation therapy will inevitably increase the risk of acute and chronic radiation damages to healthy organs. Therefore, reducing the acute and chronic radiation injuries associated with radiotherapy will promote the clinical application of radiotherapy and improve the prognosis and quality of life for cancer patients.

With the rapid development of nuclear technology and nuclear industry, nuclear energy has been widely used in industrial and agricultural production, scientific and technological research, national defense and people's wellbeing. The peaceful use of "nuclear" has become a driving force for the development of all countries in the world. Deviation from operating conditions in nuclear facilities or nuclear activities, that is, the occurrence of a nuclear accident, will cause accidental and involuntary exposure for workers and surrounding people, resulting in radiation damage. Therefore, drugs for mitigating radiation damage should be kept by near nuclear facilities.

HIg is an immunoglobulin product derived from healthy donor plasma pools by separation, purification, and virus inactivation/removal, whose main active ingredient is a combination of polyclonal immunoglobulins against various exogenous antigens and self-antigens. The human immunoglobulin according to the administration route can be divided into intravenous immunoglobulin (IVIg), intramuscular immunoglobulin (IMIg) and subcutaneous immunoglobulin (SCIg). HIg is an effective drug for the treatment of primary immunodeficiency, secondary immunodeficiency, autoimmune diseases (Kawasaki disease, idiopathic thrombocytopenic purpura), and is widely used in clinical practice.

The present inventors found that HIg had a certain therapeutic effect on radiation injuries, which was specifically shown that irradiation led to atrophy of thymus and spleen, reduction in the number of lymphocytes, shortening of the large intestine, and increase in the level of inflammation in the small intestine, as well as leading to death in mice. On the other hand, HIg helped the mice to reverse the symptoms and reduce the mortality. However, the effect of HIg is significant only in females, while its effect needs to be improved in males (patent application 202010925913.X).

Hypoxanthine, as an important alkaloid purine, is a nucleoside metabolite, which is widely distributed in the body and participates in some physiological functions. Hypoxanthine can be used as the main biochemical index of abnormal myocardial energy metabolism, and it has certain effects on asthma, bronchodilation and hypotension. Its oxidation products uric acid and oxygen free radicals also have some pharmacological effects on hyperuricemia. There are no reports that hypoxanthine is used to treat radiation injuries.

CONTENT OF THE INVENTION

The object of the present invention is to provide a combined drug that enhances the efficacy of HIg in the treatment of radiation injuries.

In the present invention, "radiation injury" refers to the injury resulted from irradiation of X-rays due to radiation therapy, accelerators, and $\alpha$, $\beta$ and/or $\gamma$ rays emitted by radioactive substances on the body, and said irradiation includes both irradiation on the surface of the body and irradiation on cells in the body after the radioactive substance enters the body.

The technical solution of the present invention is as follows:

Firstly, the present invention provides a combined drug for the treatment of radiation injury, which contains hypoxanthine and HIg;

further, said HIg includes IVIg, IMIg and/or SCIg.

Further, said combined drug is a drug that restores the hematopoietic function of the body and/or improves immunity after radiation injuries.

Further, said combined drug is a drug that retards thymic atrophy, spleen atrophy, leukocytopenia, decreased lymphocyte ratio, increased neutrophil ratio and/or inflammation caused by radiation injuries.

Further, said inflammation is intestinal inflammation.

Further, said combined drug is for male (including human and animals).

Therefore, the present invention also provides a pharmaceutical composition, which is composed of hypoxanthine and HIg, and the mass ratio of hypoxanthine to human immunoglobulin (HIg) is 1:(1-11).

Further, the mass ratio of hypoxanthine to HIg is 1:6.

The present invention also provides the use of a combined drug or a pharmaceutical composition mentioned above in the preparation of a medicament for alleviating radiation damage.

The present invention also provides a combined drug for treating tumors, which contains anti-tumor radiotherapy drugs, hypoxanthine and HIg;

further, said HIg includes IVIg, IMIg and/or SCIg.

Further, said combined drug is a drug that restores the hematopoietic function after radiotherapy.

Further, said combined drug is a drug that retards thymic atrophy, spleen atrophy, leukocytopenia, decreased lymphocyte ratio, increased neutrophil ratio and/or inflammation caused by radiotherapy.

Further, said inflammation is intestinal inflammation.

Further, said combined drug is for male (including human and animals).

The beneficial effects of the present invention include:
1) The combined drug of the present invention can be used to restore the hematopoietic function after radiation injuries;

2) The combined drug of the present invention can alleviate thymic atrophy, spleen atrophy, leukocytopenia and/or inflammation caused by radiation injuries;
3) The combined drug of the present invention can overcome the disadvantage that IVIg alone cannot effectively treat radiation injuries in male animals.

Obviously, based on the above content of the present invention, according to the common technical knowledge and the conventional means in the field, without department from the above basic technical spirits, other various modifications, alternations, or changes can further be made.

By the following specific examples of said embodiments, the above content of the present invention is further illustrated. But it should not be construed that the scope of the above subject matter of the present invention is limited to the following examples. The techniques realized based on the above content of the present invention are all within the scope of the present invention.

EXAMPLES

Exmple 1. Use of IVIg Combined with Hypoxanthine for the Treatment of Radiation Injuries 1. Method
1.1. Analysis of hematopoietic system injury by total body irradiation at 5 Gy
24 male mice were divided into two groups:
1) IVIg group, 12 mice;
2) IVIg+hypoxanthine group, 12 mice;
IVIg was administered to IVIg group within 5 min after total body irradiation, followed by injecting IVIg twice a week for two weeks at a dose of 0.3 g/kg body weight.

For IVIg+hypoxanthine group, hypoxanthine was intraperitoneally injected to mice within 30 min before total body irradiation, and then IVIg was administrated within 5 min after irradiation, followed by administrating IVIg twice a week for two weeks as well as intraperitoneally injecting hypoxanthine every two days. The dose of hypoxanthine was 50 mg/kg body weight; while the dose of IVIg was 0.3 g/kg body weight.

1.2. Analysis of Intestinal Injury by 12 Gy of Local Abdominal Irradiation
44 male mice were divided into 4 groups:
1) TAI group, 10 mice;
2) hypoxanthine group, 10 mice;
3) IVIg group, 12 mice;
4) IVIg+hypoxanthine group, 12 mice;
TAI group received only local abdominal irradiation.
Hypoxanthine was orally administered to the mice in hypoxanthine group 30 min before irradiation, followed by gavage through mouth every two days. The dose of hypoxanthine for each gavage was 50 mg/kg body weight.
IVIg was intravenously injected into the mice in IVIg group within 5 min after irradiation, followed by injection twice a week for two weeks at a dose of 0.3 g/kg body weight.
Hypoxanthine was orally administered to the mice in IVIg+hypoxanthine group 30 min before irradiation, and then IVIg was injected within 5 min after irradiation, followed by injecting IVIg twice a week for two weeks as well as gavaging hypoxanthine through mouth every two days. The dose of hypoxanthine was 50 mg/kg body weight; while the dose of IVIg was 0.3 g/kg body weight.
Then, blood was collected from mice to determine the number of leukocytes, lymphocytes and neutrophils. Spleen, thymus and large intestine were taken for observation, and the levels of IL-6 and TNF-α in small intestine were further detected.

2. Results

Figure 1:
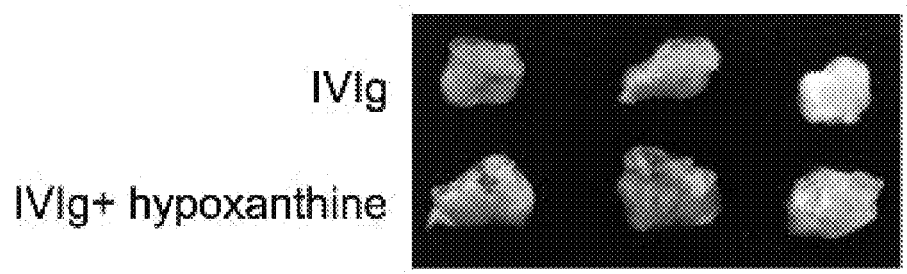
FIG. 1: The appearance of the thymus.
Figure 2:
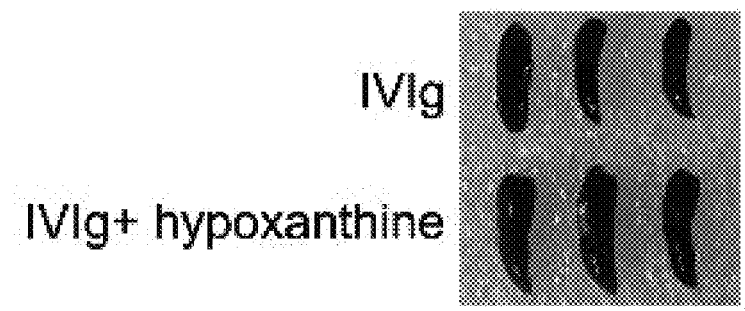
FIG. 2: The appearance of the spleen.
Figure 3:
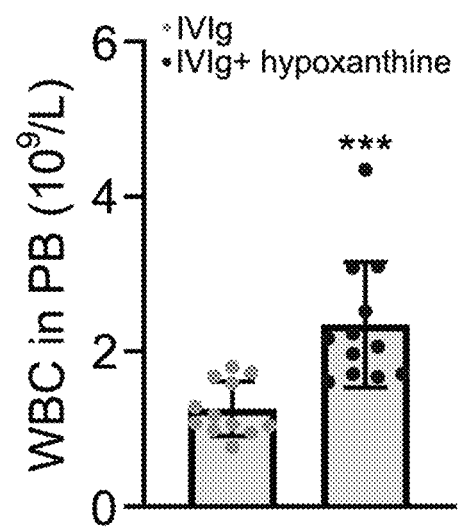
FIG. 3: Leukocyte count in peripheral blood.

It is shown that total body irradiation can cause the following abnormalities in mice: atrophy of thymus and spleen, decrease in hematopoietic function, and subsequent reduction of white blood cells. As shown in FIGS. 1-3, the volumes of thymus and spleen as well as leukocyte numbers were significantly increased in the IVIg+hypoxanthine group compared with IVIg group. The results indicated that the combination of IVIg and hypoxanthine could restore the size of thymus and spleen more obviously in mice compared with IVIg alone, and further lead to the recovery of the hematopoietic function in irradiated mice.

Figure 4:
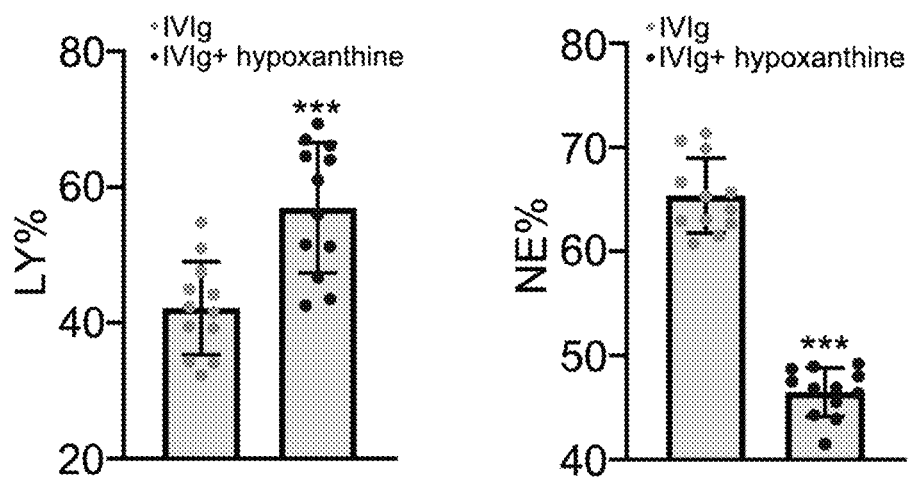
FIG. 4: Statistical analysis on lymphocyte ratio (LY %) and neutrophil ratio (NE %).
Figure 5:
FIG. 5: The appearance of the large intestine in TAI group and hypoxanthine group.
Figure 6:
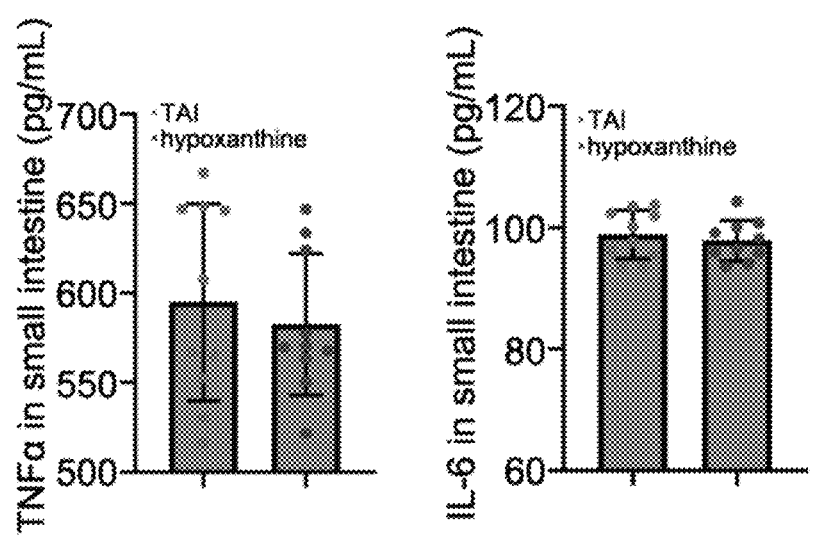
FIG. 6: Levels of TNF-α and IL-6 in the small intestine of TAI group and hypoxanthine group. The ordinate mL represents the volume of PBS used to extract TNF-α and IL-6 from the small intestine, and the volume of PBS used for each unit weight of the small intestine is consistent.
Figure 7:
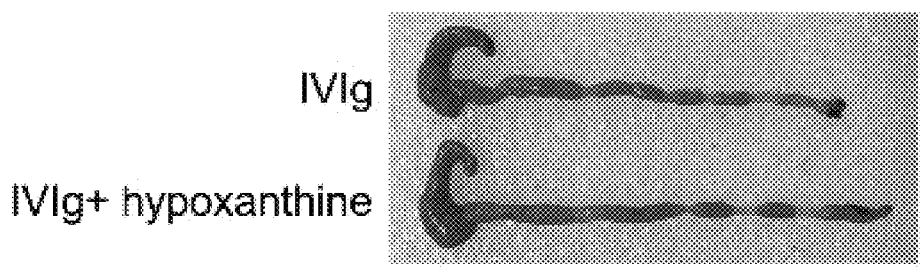
FIG. 7: The appearance of the large intestine in IVIg group and IVIg+hypoxanthine group.
Figure 8:
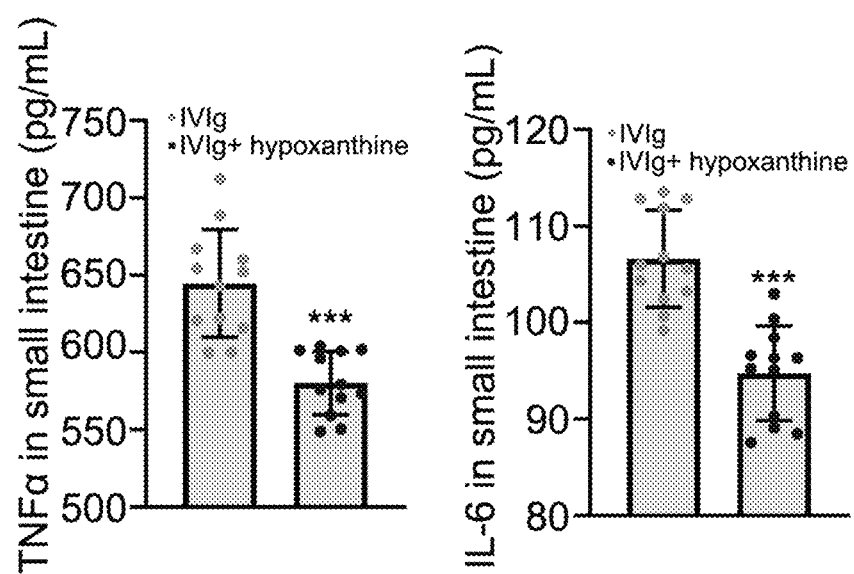
FIG. 8: Levels of TNF-α and IL-6 in the small intestine of IVIg group and IVIg+hypoxanthine group. The ordinate mL represents the volume of PBS used to extract TNF-α and IL-6 from the small intestine, and the volume of PBS used for each unit weight of the small intestine is consistent.

Radiation could cause a decrease in the level of lymphocytes and an increase in the level of neutrophils in the peripheral blood of mice. Compared with IVIg group, the ratio of lymphocyte is higher in IVIg+hypoxanthine group, while the ratio of neutrophils is lower (FIG. 4), indicating that the combination of IVIg and hypoxanthine could improve the immune function in irradiated mice. Local abdominal radiation can induce intestinal inflammation in mice, such as shortening of the large intestine and elevation of inflammatory factors TNFα and IL-6 in the small intestine (Li et al., Gut commensal derived-valeric acid protects against radiation injuries, *Gut Microbes,* 2020, 11: 789-806). Hypoxanthine alone (hypoxanthine group) could not improve the above symptoms, that is no difference in the length of the large intestine and the inflammatory factors TNFα and IL-6 in the small intestine was found between hypoxanthine group and TAI group (FIGS. 5 and 6), indicating that oral administration of hypoxanthine alone could not inhibit radiation-induced inflammation. Although IVIg may alleviate the aforementioned changes to some extent, the length of the large intestine in IVIg+hypoxanthine group was longer than that in IVIg group, and the levels of inflammatory cytokines TNFα and IL-6 in the small intestine were also lower than that in IVIg group (FIGS. 7 and 8). This suggested that compared with the single use of IVIg, the combination of IVIg and hypoxanthine could further inhibit the radiation-induced inflammation.

In summary, the combination drug of the present invention can be used to restore the hematopoietic function of the body after irradiation, and can relieve the atrophy of thymus and spleen, leukocytopenia and/or inflammation caused by irradiation; and the combination drug has overcome the disadvantage that IVIg alone cannot effectively treat male animals.

The invention claimed is:

1. A combination drug for the treatment of radiation injuries for a subject in need thereof, comprising hypoxanthine and human immunoglobulin (HIg), wherein:
   said HIg is selected from intravenous immunoglobulin (IVIg), intramuscular immunoglobulin (IMIg), subcutaneous immunoglobulin (SCIg), and mixtures thereof; and
   the mass of hypoxanthine is 50 mg/kg calculated based on the subject's weight; and
   the mass ratio of hypoxanthine to HIg is from 1:1 to 1:11.

2. The combination drug according to claim 1, wherein the combination drug restores the hematopoietic function of the body and/or improves immunity after radiation injuries.

3. The combination drug according to claim 1, wherein the combination drug mitigates thymic atrophy, spleen atrophy, leukocytopenia, decreased lymphocyte ratio, increased neutrophil ratio and/or inflammation caused by radiation injuries.

4. The combination drug according to claim 1, wherein the combination drug is for males.

5. The combination drug according to claim 1, wherein the mass ratio of hypoxanthine to HIg is 1:6.

6. A method for alleviating radiation damage, comprising administering an effective amount of a composition to a subject in need thereof, wherein the composition comprises the combination drug according to claim 1.

7. A method for treating tumors, comprising administering to a subject in need thereof an effective amount of the combination drug according to claim 1 and anti-tumor radiotherapy drugs.

8. The method according to claim 6, wherein the combination drug restores the hematopoietic function after radiotherapy, retards thymic atrophy, spleen atrophy, leukocytopenia, decreased lymphocyte ratio, increased neutrophil ratio and/or inflammation caused by radiotherapy.

9. The method according to claim 6, wherein the combination drug is for males.

* * * * *